United States Patent [19]
Koike et al.

[11] Patent Number: 4,736,744
[45] Date of Patent: Apr. 12, 1988

[54] LASER COAGULATION SYSTEM

[75] Inventors: Chikashi Koike, Hino, Japan; Stephan Pataki, Campbell, Calif.

[73] Assignees: Kowa Company Ltd., Aichi, Japan; Coherent Incorporated, Palo Alto, Calif.

[21] Appl. No.: 919,320

[22] Filed: Oct. 14, 1986

[30] Foreign Application Priority Data

Oct. 18, 1985 [JP] Japan ................. 60-231317

[51] Int. Cl.$^4$ ............................................. A61B 17/36
[52] U.S. Cl. ................................................ 128/303.1
[58] Field of Search ............ 128/4, 6, 303.1, 395–398;
219/121 L, 121 LA, 121 LS, 121 LT; 350/311, 315, 317, 318, 162.13; 362/259, 293; 354/76

[56] References Cited

U.S. PATENT DOCUMENTS

| | | | |
|---|---|---|---|
| 3,096,767 | 7/1963 | Gresser et al. | 128/395 |
| 3,710,798 | 1/1973 | Bredemeier | 128/395 |
| 4,387,989 | 6/1983 | Pirich | 350/162.13 |
| 4,520,816 | 6/1985 | Schachar et al. | 128/395 |
| 4,573,780 | 3/1986 | Sato et al. | 354/76 |
| 4,580,559 | 4/1986 | L'Esperance | 128/395 |

Primary Examiner—Max Hindenburg
Attorney, Agent, or Firm—Bruce L. Adams; Van C. Wilks

[57] ABSTRACT

A laser coagulation system projects a slit image beam into an eyeball to determine a treatment point and selectively delivers argon and krypton laser beams thereto during an opthalmological operation. Observation equipment receives the slit image beam and laser beams reflected from the treatment point to observe the treatment point. A pair of discs are coaxially rotatably mounted around a shaft parallel to the optical axis between the treatment point and the observation equipment. The discs are selected according to the kind of laser beams and disposed on the optical axis to block the reflected laser beam during the irradiation thereof and to pass the reflected slit image beam during other than the irradiation of the laser beam. One disc has a filter for absorbing the argon laser beam and an opening for passing the slit image beam, both disposed along the periphery of the disc, and the other disc has another filter for absorbing the krypton laser beam and an opening for passing the slit image beam.

16 Claims, 5 Drawing Sheets

LASER COAGULATION SYSTEM

BACKGROUND OF THE INVENTION

1. Field of the Invention

This invention relates to a laser coagulation system, and more particularly to a laser coagulation system adapted for use in an ophthalological treatment in which a laser beam from a laser source is radiated into a patient's eye to develop a large amount of heat effective to cause thermal coagulation at a predetermined portion of the biological organism in the eyeball of a patient.

2. Description of the Prior Art

There have long been known laser coagualtion systems in which during an opthalmic operation against diseases such as retina detachment, glaucoma, etc., a patient's eye is irradiated with laser energy, which is absorbed in a biological organism such as retina to develop thermal coagulation thereon for ophthalmological treatment. For this purpose, the laser coagulation system includes a laser beam projector for producing a laser beam from an argon or krypton laser, which is condensed to a laser beam of a predetermined diameter, directed toward a predetermined portion of the eyeball to be coagulated, and then focused thereon as a laser spot for thermal coagulation.

The laser coagulation system further comprises a slit image projector for forming a slit image on the eyeball to illuminate the background and to determine the predetermined portion of eyeball to be coagulated.

This type of laser coagulation system is further provided with an observation equipment for observing the slit image and the laser beam projected onto the eyeball to be coagulated. Doctors always observe the eyeball by means of the observation equipment to be able to accurately perform the laser beam projection onto the eyeball to be coagulated. Some of the laser beam is usually reflected back from the irradiated eye portion into the eyes of the doctor through the observation equipment, thus resulting in damage to his eyes.

To prevent such damage, a safety filter is provided to absorb laser energy reflected into the observation equipment.

On the other hand, it has become very typical to selectively employ two different laser beams such as argon and krypton laser beams depending upon the eye portion to be treated. Thus, two kinds of safety filters respectively corresponding to the argon and krypton laser beams are necessary.

Therefore, the prior art coagulation system has the drawback that the safety filter corresponding to the laser beam being used must be attached to the observation equipment every time it is used. This can eventually lead to a big problem in that the selection of the wrong safety filter can cause a serious injury.

SUMMARY OF THE INVENTION

It is therefore an object of the present invention to provide a laser coagulation system capable of utilizing a plurality of laser beams each differnt in a wavelength.

It is another object of the invention to provide a laser coagulation system capable of automatically bringing a corresponding safety filter into the optical path of the observation equipment in response to the selection of the laser beam.

A laser coagulation system according to the present invention comprises a laser source for selectively producing one of a plurality of laser beams each different in wavelength, a slit image projector for projecting a slit image into the eyeball to determine the selected portion to be coagulated in the eyeball, a laser beam projector for projecting selected one of the laser beams onto the selected portion to be coagulated, an observation equipment having an optical path aligned to an observer for observing the slit image and the laser beam projected onto the eyeball, and a plurality of safety filters, each corresponding to one of the laser beams and mounted within the obervation equipment for absorbing the most energy relative to the corresponding laser beam, respectively. One of the safety filters is selected and brought into the observation optical path in response to the selection of either one of the laser beams, thus absorbing a substantial part of the laser energy that is reflected into the observation equipment and reducing the reflected laser energy to a level that is safe for the observer.

Thus, according to the present invention, a safety filter corresponding to the selected laser beam is automatically brought into the optical path of the observation equipment to cut a substantial part of energy reflected back to the observer at the time the selected laser beam is being projected onto the eye portion to be coagulated.

According to the preferred embodiment of the present invention, argon and krypton laser beams are employed, and safety filters for argon and krypton laser beams are mounted on first and second coaxial discs, which are selectively rotated in response to the selection of argon or krypton laser beam to bring the safety filter for argon or krypton laser beam to the optical path of the observation equipment.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
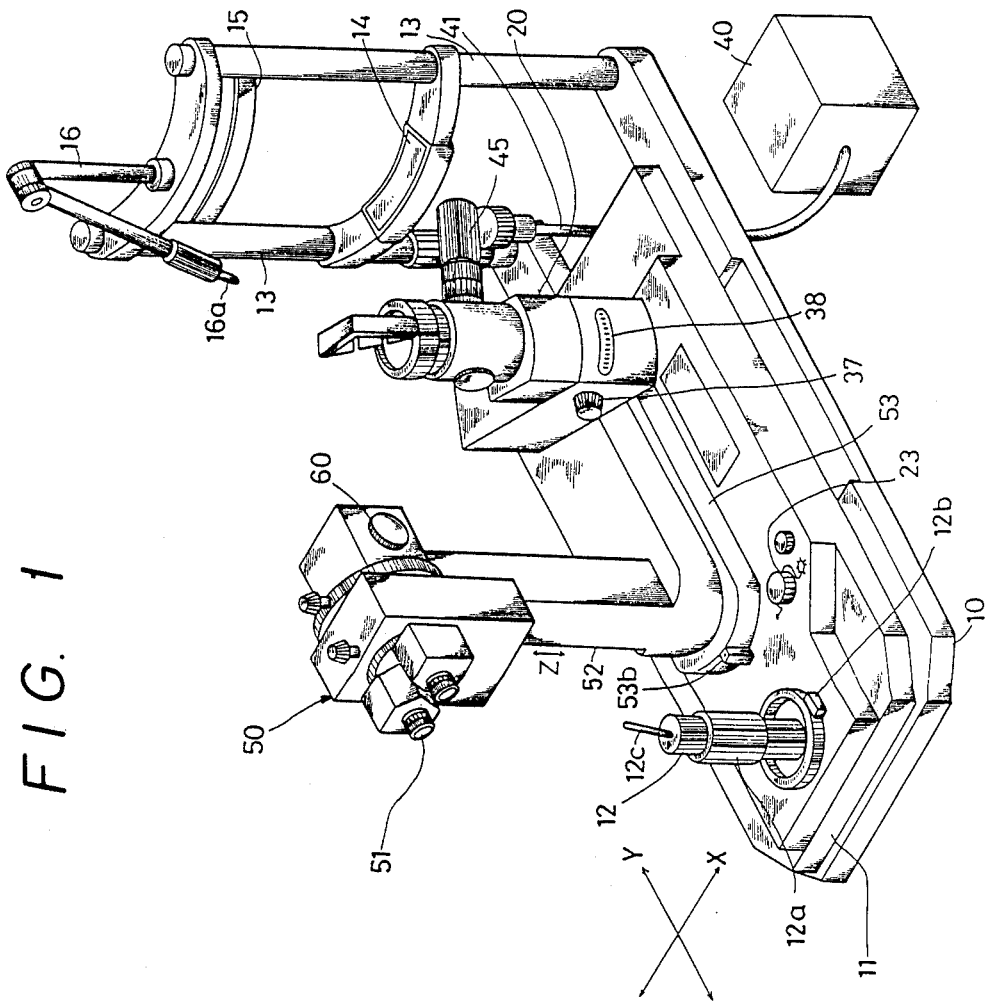
FIG. 1 is a perspective view showing a whole appearance of a laser coagulation system of the present invention.

FIG. 1 shows the appearance of a laser coagulation or laser beam delivery system according to the present invention which includes a slider 11 mounted on a base plate 10 so as to be slidable relative to the base plate 10 in a direction X or Y by means of a manipulator 12 such as a joy stick. The displacement of the slider 11 relative to the base plate 10 can be effected by operating the manipulator 12 in the directions X and Y. The slider 11 supports thereon an instrument base 53 on which a slit image projector 20, a laser beam projector 21 and an observation equipment 50 are mounted as will be fully described later. The manipulator 12 is further provided with a handle 12a, the rotation of which allows the instrument base 53 to move upwardly or downwardly to displace the projectors 20 and 21 together with the observation equipment 50 vertically. Thus, the manipulator 12 can adjust the position of the instrument base 53 in the directions X and Y and in the vertical direction. The thus adjusted slider 11 can be locked on the base plate 10 by means of a lock 12b.

The base plate 10 has on its front edge two poles 13 between which a chin support 14 and a forehead pad 15 are fixedly mounted. A patient sits down in front of the apparatus with his chin against the support 14 and his forehead against the pad 15 and watches an eye fixation lamp 16a which serves to fix the patient's eye during measurement or coagulation.

Mounted on the rear end of the slider 11 is the slit image projector 20 which is pivotable about the axis A (see FIG. 2) and irradiates an illuminating beam to project a slit image onto the eyeball to illuminate the background and determine the portion of the eye to be measured or coagulated or the treatment point. As will be described later, the slit image projector 20 is arranged coaxially with the laser beam projector 21 for projecting a laser beam from a source 40 such as an argon or krypton laser through an optical fiber 41 onto that portion to be coagulated in the eyeball. The observation equipment for observing the focussed laser beam or imaged slit in the eyeball is further arranged on the front edge of the slider 11 so as to be rotatable about the same axis as the turning axis A for the slit image projector 20.

Figure 2:
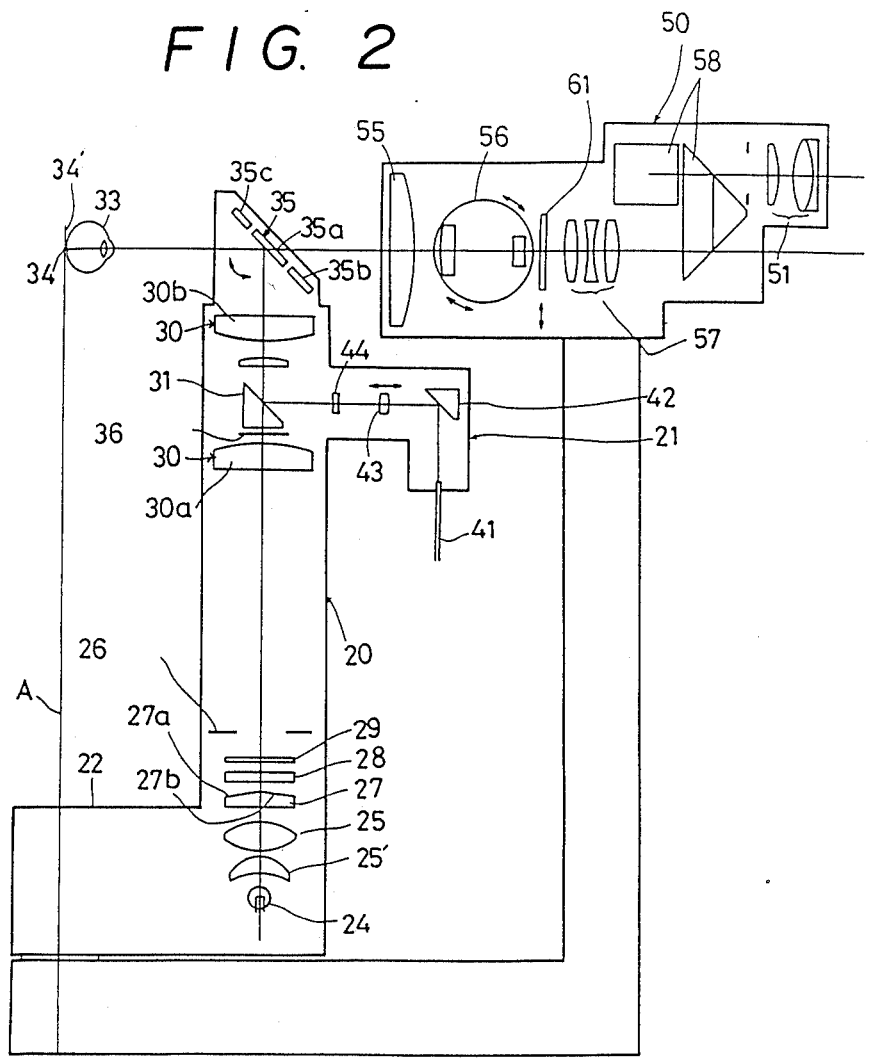
FIG. 2 is an illustrative view showing the arrangement of an optical system for a laser beam projector, slit image projector and observation equipment used in the laser coagulation system of the present invention.
Figure 3:
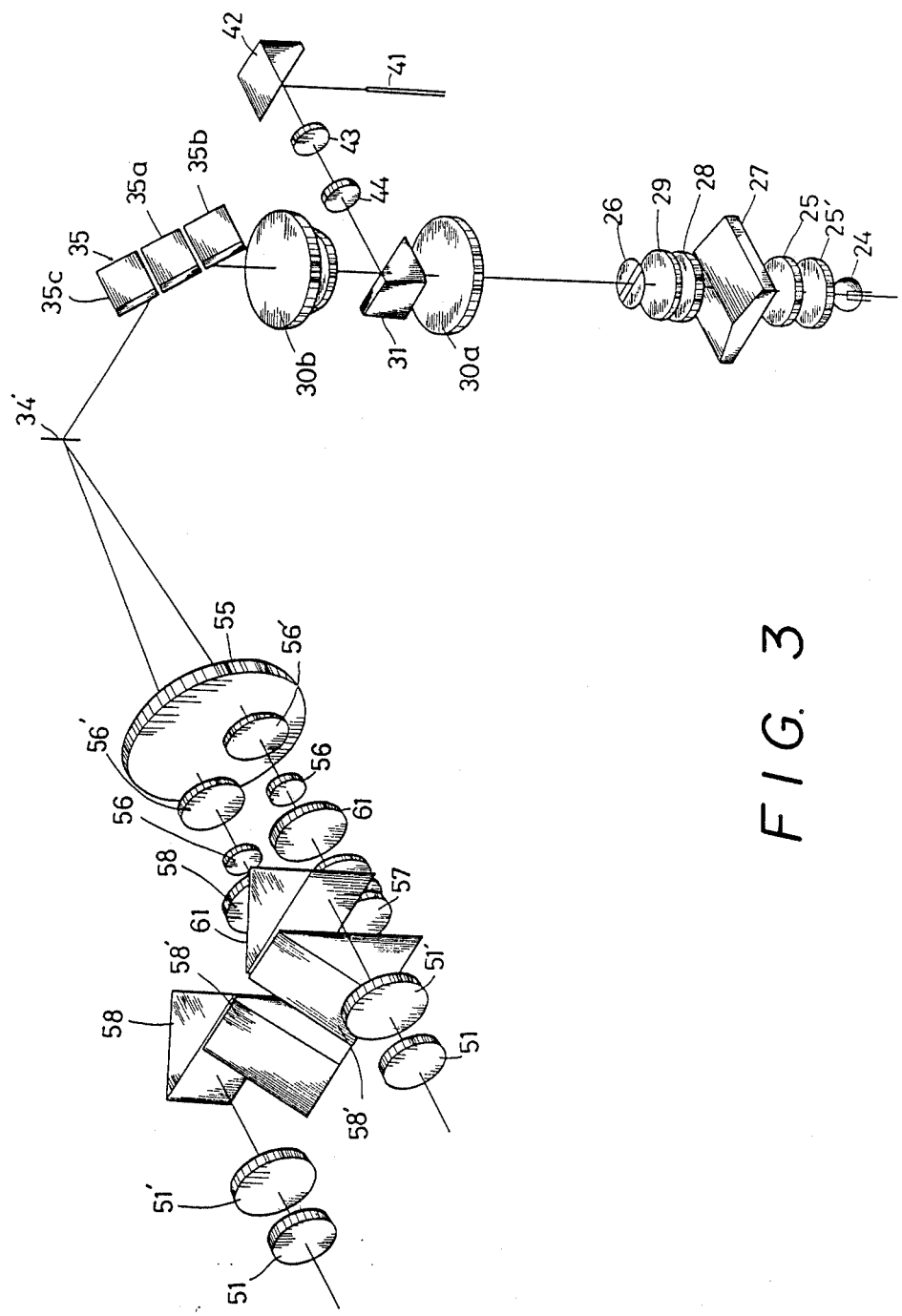
FIG. 3 is a perspective view showing the arrangement of the optical system in FIG. 2.

FIGS. 2 and 3 show the detailed arrangement of an optical system for the laser beam projector 21, slit image projector 20 and observation equipment 50. The slit image projector 20 is arranged in a housing 22 mounted so as to be rotatable about the axis A and is provided therein with a lamp 24 which is adjustable in intensity by means of an adjusting knob 23 (see FIG. 1). The lamp 24 emits illuminating light beam, which is converged by condensor lenses 25 and 25' to illuminate a slit aperture 26. Arranged between the condenser lens 25 and slit aperture 26 are a roof-shaped prism 27, an infrared ray cutting filter 28 and a detachable blue filter 29. The illuminated slit aperture 26 is imaged, for example, onto a retina 34 of a patient's eye 33 as a slit image 34' by means of a focussing lens 30 including lenses 30a and 30b. To eliminate the imaging function of the eye itself, a special contact lens (not shown) is attached to the patient's eye. A mirror assembly 35 having three-divided mirror portions 35a to 35c is mounted between the patient's eye 33 and lens 30b. The central mirror portion 35b can, as described later, be turned upwardly, downwardly, leftwardly or rightwardly about an axis perpendicular to or within the paper surface (in FIG. 2) by means of an operating lever 12c of the manipulator 12.

Arranged between the lens 30a and a prism 31 is a screen plate 36 which serves to interrupt the arrival of slit light to the central mirror 35a, while permitting it to reach the upper and lower mirrors 35b, 35c to the retina 34. To make the slit image on the retina 34 brighter and sharper, the deflection prism 27 has one surface 27a angled to deflect light toward the lower mirror 35b and the other surface 27b also angled to deflect light toward the upper mirror 35c. Thus, the deflection prism functions to form the filament image of the lamp 24 at two points existing on the entrance pupil of the focussing lens 30.

It is to be noted that the slit width and length of the slit aperture 26 are adjustable by adjusting knobs 37 and 38 and the intensity of the lamp 24 is adjustable by an adjusting knob 23.

The laser beam projector 21 is, on the other hand, arranged in the same housing 22 as the slit image projector 20. The laser beam passing through the optical fiber 41 from the laser source 40 is deflected rectangularly at a prism 42 toward a variator lens 43 and a lens 44, reflected at the prism 31 and then advanced along the same optical path or axis as the slit image projector 20 through the lens 30b, mirror 35a and contact lens to radiate the laser spot of a predetermined diameter on the retina 34 for thermal coagulation. The spot diameter of the laser beam can be adjusted in the range of about 50 μm to 1 mm by turning a knob 45 and adjusting the variator lens 43.

The instrument base 53 (FIG. 1) is provided with the housing 22 for accommodating the projectors 20 and 21 and a housing 52 for accommodating the observation equipment 50, and is displaceable vertically using the handle 12a of the manipulator 12 as mentioned before. Further, the housings 22 and 52 are turnable to each other about the axis A. so that the projectors 20, 21 and the observation equipment 50 can effect upward, downward or turning movement, respectively. The observation equipment 50 includes an optical system comprised of an objective 55, variator lenses 56 and 56', a safety filter 61, a focussing lens 57, erecting prisms 58 and 58', and eyepieces 51, 51'. The observation equipment 50 allows the observation of the slit image and laser spot formed in the eyeball. The adjustment of a knob 60 causes the variator lens 56 to be adjusted to provide an enlarged or reduced slit image or laser spot. The safety filter 61 is used to interrupt the laser beam reflected back from the irradiated portion of eye or cornea and protect the eyes of an observer. For this purpose, the safety filter 61 is automatically inserted into the optical path of the observation equipment 50 immediately before the laser source 40 is activated to produce a stronger laser beam.

It should be noted that the optical elements following the objective 55 are provided in pairs respectively to allow binocular observation.

Figure 4:
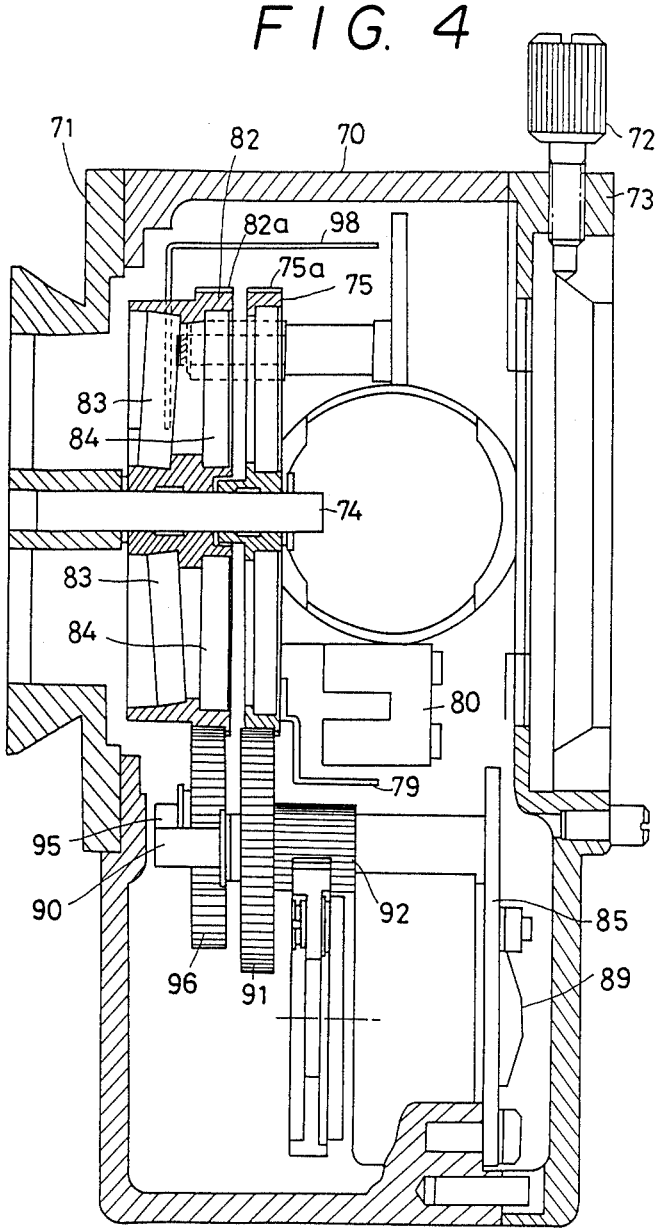
FIG. 4 is a cross-sectional view showing the structure of a safety filter assembly as viewed in the direction parallel to the optical path of the observation equipment.
Figure 5:
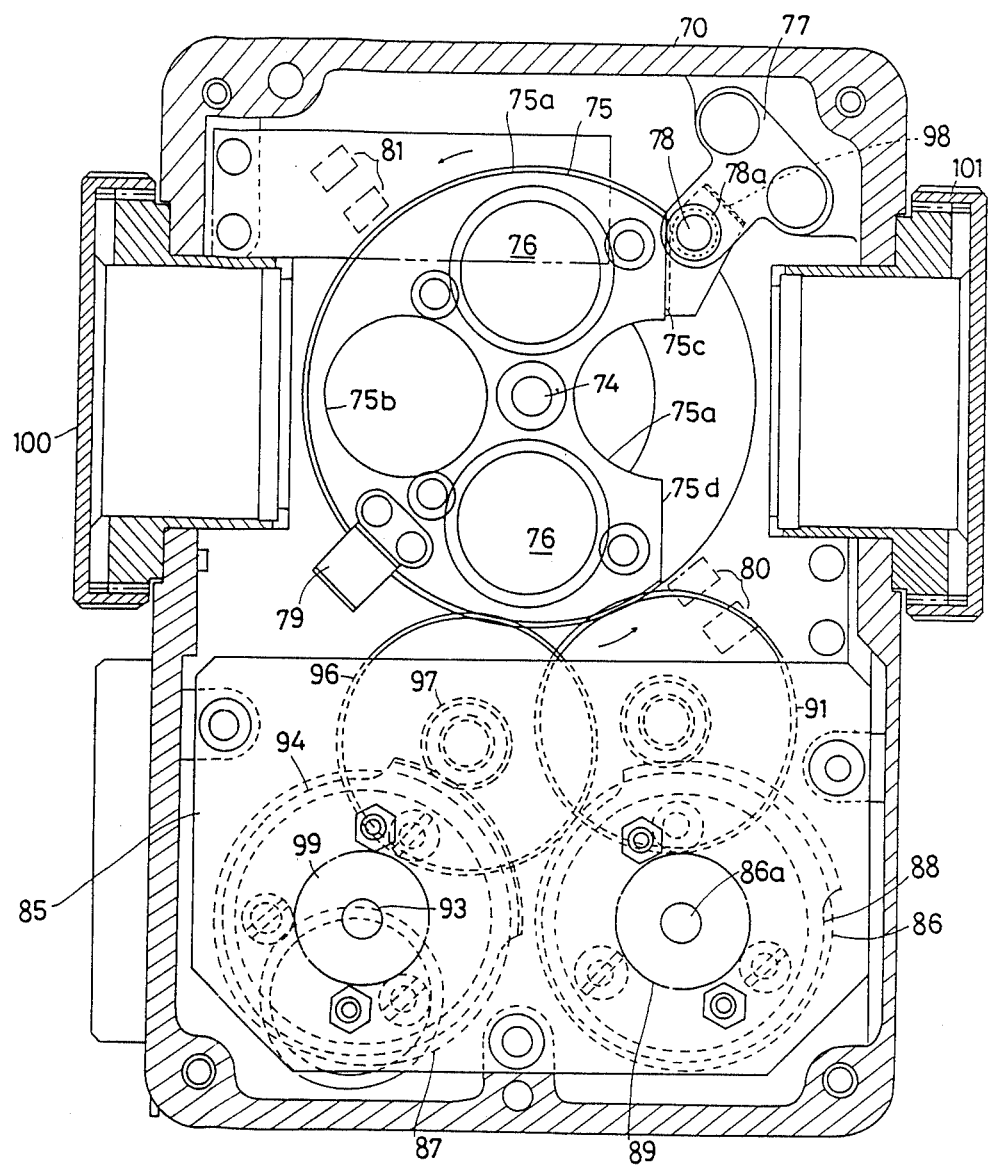
FIG. 5 is a cross-sectional view showing the structure of a safety filter assembly as viewed in the direction perpendicular to the optical path of the observation equipment.

Reference is now made to FIGS. 4 and 5 to describe the structure of the safety filter assembly 61 in detail.

FIG. 4 shows in cross section a side face of the safety filter assembly as viewed in the same direction as in the observation equipment 50 in FIG. 2 with optical elements such as the objective 55, imaging lens 57, etc. being removed therefrom. In FIG. 4, the safety filter assembly is accommodated in a housing 70 on one side of which an adapter 71 is provided for connection to a housing for the objective lens 55 and variator lens 56 (FIG. 2). On the other side of the housing 70, another adapter 73 is provided for accommodating the imaging lens 57 which is fixed thereto by a screw 72.

The adapter 71 is also provided therein with a shaft 74 extending parallel relative to the optical axis into the housing 70 in which the shaft 74 rotatably carries an optical disc 75 bearing argon filters. The disc 75 is, as shown in FIG. 5, horseshoe-shaped and formed thereon with aperture means in the form of a semicircular cutout 75a and a circular opening 75b which are arranged symmetrically with respect to the shaft 74 and come into alignment with the optical path to the eyepiece 51. The disc 75 carries argon filters 76 along a line perpendicular to the diametric line connecting the centers of the cutout 75a and opening 75b, the cutout 75a and opening 75b existing on the circumference of a circle about the shaft 74.

The disc 75 further has straight portions 75c and 75d which extend to the cutout 75a and come into contact with a pin 78 fixed to the housing 70 through a bracket 77 to limit rotation of the disc 75 in clockwise and counterclockwise directions, respectively. The pin 78 is provided on its circumference with an elastic member 78a for absorbing impact due to contact of the pin 78 with the portions 75c and 75d.

The disc 75 is further provided with a photointerrupter 79 extending upwardly from the disc's surface and diametrically opposed to the pin 78. The photointerrupter 79 is, as shown in FIG. 4, L-shaped and constructed to be able to pass through a photocoupler 80 for the argon laser and a photocoupler 81 for the krypton laser which are spaced diametrically relative to a line connecting the pin 78 and photointerrupter 79. The disc 75 is formed with a gear portion 75a on its whole circumference except for the cutout 75a and straight portions 75c and 75d.

On the shaft 74 there is rotatably mounted another disc 82 which is coaxially substantially the same in shape as disc 75, but thicker and provided with krypton filters 83 and 84 which are arranged in pairs at the same positions as the filters on the other disc 75, and one pair of which is inclined relative to the other pair of filters at an angle of about 10 degrees to scatter a part of the krypton laser back to the other for reflection therebetween, thereby weakening its energy. This disc 82 is also formed with a gear portion 82a on its circumference.

The observation equipment 50 is, on the other hand, provided in the housing 70 with a rotary solenoid 86 for the argon laser filter and a rotary solenoid 87 for the krypton laser filter 87, both of which are mounted on a support 85 fixed to the housing 70.

The rotary solenoid 86 is provided with an output shaft 86a to which a gear 88 with a non-toothed portion is fixed and to which a return spring 89 is also mounted. The gear 88 engages with a pinion gear 92 integral with a gear 91 which is rotatably mounted on a shaft 90 to come into engagment with the gear 75a of the disc 75 for the argon filter.

The other rotary solenoid 87 is provided with an output shaft 93 to which a gear 94 with a non-toothed portion is fixed and to which a return spring 99 is fixed. The gear 94 engages with a pinion gear 97 integral with a gear 96 which is rotatably mounted on a shaft 95 to come into engagement with the gear 82a of the disc 82 for the krypton filters.

It is to be noted that the disc 82 is provided with a photo-interrupter 98 which extends perpendicularly to the disc surface and is phase-shifted by 180 degrees relative to the photo-interrupter 79 for the argon disc 75.

The operation of the laser coagulation system according to the present invention will now be described.

The patient first sits down with his chin against the support 14 and his forehead against the pad 15 and watches the eye fixation lamp 16. he lamp 24 of the slit image projector 20 is then turned on to form the slit image 34' on the retina 34 of the patient's eye 33 through the contact lens set thereon. The slit light has its central flux inhibited to arrive at the central mirror 35a by means by the screen plate 36 and is reflected only at the upper and lower mirrors 35b and 35c to form the slit image 34' on the retina 34. In this case, the deflection prism is used to deflect the slit light towards the mirrors 35b and 35c effectively. The intensity of the slit image can be adjusted by the knob 23, and the slit width and length can be adjusted by the adjusting knobs 37 and 38.

If the slit image 34' deviates from the desired place in the above-mentioned slit image formation, the manipulator 12 may be operated to displace the slider 11 and the housings 22 and 52 in the directions X, Y and Z and turn the projectors 20, 21 or observation equipment 50 about the axis A relative to each other until the slit image is formed on the desired portion for coagulation.

The thus formed slit image 34' can be observed by the optical system of the observation equipment including the objective 55, variator lens 56, imaging lens 57, erecting prism 58 and eyepiece 51. After the portion of eye to be coagulated has been determined, the laser source 40 is activated to emit a week laser beam, which is caused to pass through the prism 42, variator lens 43, lens 44, prism 31, and lens 30b, reflected at the central mirror 35a and then focussed as a spot onto the retina 34. For coagulation, a stronger laser beam is generated from the laser source 40 by changing power. When the stronger beam is activated, the safety filter is automatically inserted into the optical path of the observation equipment 50 to protect the eyes of the observer from the laser beam reflected at the irradiated portion of the patients eye or retina.

For fine and precise coagulation, the laser spot on the retina 34 can be displaced by scanning the central mirror 35a vertically or horizontally, that is, in the direction X or Y using the operating lever 12c of the manipulator 12.

When the laser beam is not being projected, the shutter (not shown) provided on the side of the laser source 40 is closed and discs 72 and 82 for the argon and krypton filters take a positon as shown in FIG. 5 where the return springs 88 and 99 return the rotary solenoids 86, 87 and the gears 88, 94 to their respective starting positions.

In the position shown in FIG. 5, the disc 75 is stopped with its straight portion 75c against the pin 78, and the cutout 75a and opening 75b come into the binocular optical path of the eyepieces 51 to allow the observer to observe the eyeball illuminated by the slit image projector 20. The disc 82 for the krypton laser takes the same position as the disc 75 for the argon laser although the former is not visible in FIG. 5.

If, on the other hand, an argon laser beam is to be projected by the laser beam projector 21, a switch (not shown) on the console panel is operated to activate the rotary solenoid 86 and turn the gear 89 counterclockwise in FIG. 5. This causes the clockwise roation of the gear 91 and counterclockwise rotation of the disc 75.

The counterclockwise rotation of the disc 75 by 90 degrees in FIG. 5 now causes the straight portion 75d of the disc 75 to come into contact with the pin 78 which stops its rotation. At this time, the photo-interrupter 79 passes through the photocoupler 80 to produce a detecting signal indicating that the argon filters 76 have interrupted the optical path for observation. The above-mentioned shutter is made open to permit the projection of the argon laser beam only when the detecting signal is produced. This state continues throughout the activation of the laser beam.

When the projection of the argon laser beam is terminated, the rotary solenoid 86 returns to the starting position with the disc 75 also returned to the position shown in FIG. 5.

For krypton laser projection, the disc 82 functions similarly to the disc 75 with only the difference being that the rotary solenoid 87 is activated instead of the rotary solenoid 86. The detection of rotation of the disc 82 by 90 degrees is made in cooperation with the photocoupler 81 and photo-interrupter 98.

The selection of the argon or krypton laser depends upon the condition or state of a portion to be irradiated, and the selected laser beam is projected as a spot causing no harm with very little energy.

In FIG. 5, blind covers, as indicated by reference numerals 100 and 101, are provided. These covers can be removed, if necessary, so that an optical bypass system can be attached to allow observation by a third party.

In the above-mentioned embodiments, two kinds of laser beam have been described, but it will be appreciated that more than three kinds of laser beam are also applicable. Furthermore, it will be apparent that pulse or DC motors can be employed instead of the rotary solenoids mentioned above.

While the invention has been described with reference to a preferred embodiment, it will be understood by those skilled in the art that various changes may be made and equivalents may be substituted for elements thereof without departing from the scope of the invention. In addition, many modifictaions may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. A laser coagulation system for use in an ophthalmological treatment in which a laser beam is radiated into an eyeball of a patient to generate heat effective to cause thermal coagulation at a selected portion in the eyeball, comprising:
    a laser source for selectively producing first and second laser beams each different in wavelength;
    a slit image projector for projecting a slit image into an eyeball to determine a selected portion to be coagulated in the eyeball;
    a laser beam projector for projecting a selected one of the first and second laser beams onto the selected portion to be coagulated in the eyeball;
    observation equipment having an optical path to enable an observer to observe tha slit image and the selected laser beam reflected from the eyeball along the optical path;
    a first disc rotatably mounted in the observation equipment and having thereon at least one opening for introducing the slit image along the optical path to the observer and at least one safety filter for absorbing a substantial amount of the energy of the refelcted first laser beam;
    a second disc roatably mounted in the observation equipment and having thereon at least one opening for introducing the slit image along the optical path to the observer and at least one safety filter for absorbing a substantial amount of the energy of the reflected second laser beam, each of the first and second discs being operative to rotate so that the opening thereof is positioned in the optical path in an observation mode in which the selected portion to be coagulated is determined and the safety filter is positoned in the optical path in a coagulated mode in which the coagulation is carried out; and
    means for operating the first disc at the time of selection of the first laser beam and for operating the second disc at the time of selection of the second laser beam.

2. A laser coagulation system according to claim 1; further comprising first and second photo-interrupters associated with the first and second discs, respectively, for detecting whether the opening or the safety filter is positioned in the optical path so that the laser beam is prevented from being transmitted into the eyeball when the opening is brought into the optical path.

3. A laser coagulation system according to claim 2; wherein each of the first and second discs includes a pair of openings disposed in diametrically opposed relation and a pair of safety filters disposed in diametrically opposed relation, said openings and safety filters being alternately arranged circumferentially in equally spaced apart relation.

4. A laser coagulation system according to claim 1; wherein each of the first and second discs includes a pair of openings disposed in diametrically opposed relation and a pair of safety filters disposed in diametrically opposed relation, said openings and safety filters being alternatively arranged circumferentially in equally spaced apart relation.

5. A laser coagulation system according to claim 1; wherein the first and second discs are coaxially mounted in the observation equipment.

6. In a laser beam delivery system having irradiating means for selectively irradiating one of a plurality of laser beams of different wavelength along an optical axis onto a treatment point during surgical operation, illuminating means operative to direct an illuminating beam along the optical axis onto the treatment point for illuminating the same, and observing means operative to receive the laser beam and illuminating beam reflected from the treatment point and reversely transmitted along the optical axis for observing the treatment point: a plurality of driveable controlling means selectively disposed between the treatment point and the observing means along the optical axis for controlling the transmission of the reflected laser beam and illuminating beam; selecting means for selecting one of the controlling means according to the wavelength of the selected laser beam; and driving means operative during the irradiation of the selected laser beam for driving the selected controlling means to enable the same to block the transmitted laser beam and operative during other than the irradiation of the selected laser beam for driving the selected controlling means to enable the same to pass the transmitted illuminating beam.

7. A laser beam delivery system according to claim 6; wherein the plurality of controlling means comprises a plurality of optical discs, and a shaft disposed parallel to the optical axis for coaxially rotatably mounting the optical discs to position a periphery of each optical disc on the optical axis.

8. A laser beam delivery system according to claim 7; wherein each optical disc has along the periphery thereof filtering means for filtering laser beam of specific wavelength to absorb the same and aperture means for passing therethrough the illuminating beam.

9. A laser beam delivery system according to claim 8; wherein the filtering means comprises a pair of filters disposed in diametrically opposed relation to each other, and the aperture means comprises a pair of openings disposed in diametrically opposed relation to each other so that the filters and the openings can be selectively placed on a binocular optical axis in response to the rotation of the disc.

10. A laser beam delivery system according to claim 7; including a plurality of driving means for independently rotating corresponding optical discs.

11. A laser beam delivery system according to claim 10; wherein each driving means comprises a rotary solenoid for determining the angular position of the optical disc to selectively block the laser beam and pass the illuminating beam, and a gear train engaged between the optical disc and the rotary solenoid for transmitting the rotation of the rotary solenoid to the optical disc.

12. A laser beam delivery system according to claim 10; wherein the selecting means comprises means for selecting one of the driving means according to the selected laser beam.

13. A laser beam delivery system according to claim 8; wherein detecting means for detecting the angular position of the selected optical disc to prohibit the irradiation of the laser beam when the aperture means is disposed on the optical axis.

14. A laser beam delivery system according to claim 13; wherein the detecting means comprises photo-interrupters disposed on respective ones of the optical discs for interrupting a photo-coupler of the irradiating means.

15. A laser beam delivery system according to claim 6; wherein the irradiating means comprises means for selectively irradiating one of argon and krypton laser beams.

16. A laser beam delivery system according to claim 6; wherein the illuminating means comprises a slit image projector for projecting a slit image onto a treatment area to determine a treatment point.

* * * * *